US007863276B2

(12) United States Patent
Bennett et al.

(10) Patent No.: US 7,863,276 B2
(45) **Date of Patent: *Jan. 4, 2011**

(54) SALTS OF MODULATORS OF PPAR AND METHODS OF TREATING METABOLIC DISORDERS

(75) Inventors: Dennis A. Bennett, Eureka, MO (US); Stephan D. Parent, West Lafayette, IN (US); David T. Jonaitis, Lafayette, IN (US)

(73) Assignee: KALYPSYS, Inc, San Diego, CA (US)

( * ) Notice: Subject to any disclaimer, the term of this patent is extended or adjusted under 35 U.S.C. 154(b) by 751 days.

This patent is subject to a terminal disclaimer.

(21) Appl. No.: 11/552,134

(22) Filed: Oct. 23, 2006

(65) Prior Publication Data

US 2007/0093504 A1 Apr. 26, 2007

Related U.S. Application Data

(60) Provisional application No. 60/730,249, filed on Oct. 25, 2005.

(51) Int. Cl.
*A61K 31/497* (2006.01)
*C07D 241/08* (2006.01)

(52) U.S. Cl. ................................. 514/252.12; 544/383

(58) Field of Classification Search ................. 544/383; 514/252.12

See application file for complete search history.

(56) References Cited

U.S. PATENT DOCUMENTS 4,237,130 A 12/1980 Cragoe, Jr.
5,464,788 A 11/1995 Bock et al.
5,756,504 A 5/1998 Bock et al.
6,465,468 B1 10/2002 Baxter et al.
6,673,799 B1 1/2004 Taniguchi et al.
6,852,718 B2 2/2005 Burkamp
6,939,875 B2 9/2005 Auerbach
7,494,999 B2 * 2/2009 Noble et al. ........... 514/255.02
2004/0180925 A1 9/2004 Matsuno et al.
2004/0224957 A1 11/2004 Sharma et al.
2005/0070532 A1 3/2005 Liu et al.
2005/0107445 A1 5/2005 Watkins et al.
2005/0124625 A1 6/2005 Salvati et al.
2005/0153981 A1 7/2005 Li et al.
2005/0203151 A1 9/2005 Malecha et al.
2005/0234046 A1 10/2005 Zhao
2006/0167012 A1 7/2006 Noble
2006/0199820 A1 9/2006 Bannen
2006/0205736 A1 * 9/2006 Noble et al. ........... 514/255.02
2006/0258683 A1 11/2006 Liu
2007/0190079 A1 8/2007 Shiau et al.
2007/0219193 A1 9/2007 Zhao
2007/0249519 A1 10/2007 Guha et al.
2008/0004281 A1 1/2008 Rao et al.
2008/0176861 A1 7/2008 Guha et al.
2008/0287477 A1 11/2008 Malecha et al.
2009/0029971 A1 * 1/2009 Noble et al. ................ 514/218
2009/0143396 A1 6/2009 Malecha et al.

FOREIGN PATENT DOCUMENTS

EP 0107622 A1 5/1984
EP 0158596 A2 10/1985
EP 0173899 A2 3/1986
EP 00548798 A1 12/1991
EP 1236719 A1 9/2002
JP 20011261657 2/2007
WO WO9725042 A1 7/1997
WO WO9857949 A1 12/1998
WO WO9937304 A1 7/1999
WO WO0012074 A2 3/2000
WO WO0056704 A1 9/2000
WO WO0174797 A1 10/2001
WO WO02100822 A1 12/2002
WO WO03082288 A1 10/2003
WO WO2004073606 A2 9/2004
WO WO2004092117 A1 10/2004
WO WO2004092130 A2 10/2004
WO WO2004093879 A1 11/2004
WO 2005016881 A1 2/2005
WO WO2005011653 A2 2/2005
WO WO2005011654 A2 2/2005
WO WO2005011656 A2 2/2005
WO WO2005011657 A2 2/2005
WO WO2005040136 A1 5/2005
WO WO2005044797 A1 5/2005
WO WO2005060958 A1 7/2005

(Continued)

OTHER PUBLICATIONS

Sulfonyl-Substituted Bicyclic Compounds As Modulators of PPAR, U.S. Appl. No. 12/204,489, filed Sep. 4, 2008, unpublished.

(Continued)

*Primary Examiner*—James O Wilson
*Assistant Examiner*—Ebenezer Sackey
(74) *Attorney, Agent, or Firm*—Dennis A. Bennett; Cynthia Hathaway

(57) ABSTRACT

Salt forms of potent modulators of peroxisome proliferator activated receptors, pharmaceutical compositions comprising the same, and methods of treating disease using the same are disclosed.

9 Claims, No Drawings

FOREIGN PATENT DOCUMENTS

| | | | |
|---|---|---|---|
| WO | WO9525443 | A1 | 9/2005 |
| WO | WO2005115983 | A1 | 12/2005 |
| WO | WO2006014168 | A1 | 2/2006 |
| WO | WO2006034279 | A1 | 3/2006 |
| WO | WO2006034312 | A1 | 3/2006 |
| WO | WO2006034315 | A2 | 3/2006 |
| WO | WO2006034338 | A1 | 3/2006 |
| WO | WO2006034341 | A2 | 3/2006 |
| WO | WO2006034440 | A2 | 3/2006 |
| WO | WO2006034441 | A1 | 3/2006 |
| WO | WO2006034446 | A2 | 3/2006 |
| WO | 2006055187 | | 5/2006 |
| WO | 2007047432 | A1 | 4/2007 |
| WO | 2008043024 | | 4/2008 |

OTHER PUBLICATIONS

Sulfonyl-Substituted Bicyclic Compounds As Modulators of PPAR, U.S. Appl. No. 12/396,513, filed Mar. 3, 2009, unpublished.

* cited by examiner

SALTS OF MODULATORS OF PPAR AND METHODS OF TREATING METABOLIC DISORDERS

This application claims the benefit of priority of U.S. provisional Application No. 60/730,249 Filed Oct. 25, 2005, the disclosure of which is hereby incorporated as if written herein in its entirety.

FIELD OF THE INVENTION

The present invention relates to salts and methods for treating various diseases by modulation of nuclear receptor mediated processes using these salts, and in particular processes mediated by peroxisome proliferator activated receptors (PPARs).

BACKGROUND OF THE INVENTION

Peroxisome proliferators are a structurally diverse group of compounds which, when administered to mammals, elicit dramatic increases in the size and number of hepatic and renal peroxisomes, as well as concomitant increases in the capacity of peroxisomes to metabolize fatty acids via increased expression of the enzymes required for the β-oxidation cycle (Lazarow and Fujiki, *Ann. Rev. Cell Biol.* 1:489-530 (1985); Vamecq and Draye, *Essays Biochem.* 24:1115-225 (1989); and Nelali et al., *Cancer Res.* 48:5316-5324 (1988)). Compounds that activate or otherwise interact with one or more of the PPARs have been implicated in the regulation of triglyceride and cholesterol levels in animal models. Compounds included in this group are the fibrate class of hypolipidemic drugs, herbicides, and phthalate plasticizers (Reddy and Lalwani, *Crit. Rev. Toxicol.* 12:1-58 (1983)). Peroxisome proliferation can also be elicited by dietary or physiological factors such as a high-fat diet and cold acclimatization.

Biological processes modulated by PPAR are those modulated by receptors, or receptor combinations, which are responsive to the PPAR receptor ligands. These processes include, for example, plasma lipid transport and fatty acid catabolism, regulation of insulin sensitivity and blood glucose levels, which are involved in hypoglycemia/hyperinsulinemia (resulting from, for example, abnormal pancreatic beta cell function, insulin secreting tumors and/or autoimmune hypoglycemia due to autoantibodies to insulin, the insulin receptor, or autoantibodies that are stimulatory to pancreatic beta cells), macrophage differentiation which lead to the formation of atherosclerotic plaques, inflammatory response, carcinogenesis, hyperplasia, and adipocyte differentiation.

Subtypes of PPAR include PPAR-alpha, PPAR-delta (also known as NUC1, PPAR-beta, and FAAR) and two subtypes of PPAR-gamma. These PPARs can regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signaling cascade and lipid homeostasis (H. Keller and W. Wahli, *Trends Endoodn. Met.* 291-296, 4 (1993)).

Insight into the mechanism whereby peroxisome proliferators exert their pleiotropic effects was provided by the identification of a member of the nuclear hormone receptor superfamily activated by these chemicals (Isseman and Green, Nature 347-645-650 (1990)). The receptor, termed PPAR-alpha (or alternatively, PPARα), was subsequently shown to be activated by a variety of medium and long-chain fatty acids and to stimulate expression of the genes encoding rat acyl-CoA oxidase and hydratase-dehydrogenase (enzymes required for peroxisomal β-oxidation), as well as rabbit cytochrome P450 4A6, a fatty acid ω-hydroxylase (Gottlicher et al., Proc. Natl. Acad. Sci. USA 89:4653-4657 (1992); Tugwood et al., EMBO J 11:433-439 (1992); Bardot et al., Biochem. Biophys. Res. Comm. 192:37-45 (1993); Muerhoff et al., J Biol. Chem. 267:19051-19053 (1992); and Marcus et al., Proc. Natl. Acad Sci. USA 90(12):5723-5727 (1993).

Activators of the nuclear receptor PPAR-gamma (or alternatively, PPARγ), for example troglitazone, have been clinically shown to enhance insulin-action, to reduce serum glucose and to have small but significant effects on reducing serum triglyceride levels in patients with Type 2 diabetes. See, for example, D. E. Kelly et al., *Curr. Opin. Endocrinol. Diabetes,* 90-96, 5 (2), (1998); M. D. Johnson et al., *Ann. Pharmacother.,* 337-348, 32 (3), (1997); and M. Leutenegger et al., *Curr. Ther. Res.,* 403-416, 58 (7), (1997).

The third subtype of PPARs, PPARδ (PPARδ, NUC1), is broadly expressed in the body and has been shown to be a valuable molecular target for treatment of dyslipidemia and other diseases. For example, in a recent study in insulin-resistant obese rhesus monkeys, a potent and selective PPARδ compound was shown to decrease VLDL and increase HDL in a dose response manner (Oliver et al., Proc. Natl. Acad. Sci. U.S.A. 98: 5305, 2001). Also, in a recent study in wild-type and HDL-lacking, ABCA $1^{-/-}$ mice, a different potent and selective PPARδ compound was shown to reduce fractional cholesterol absorption in the intestine, and coincidently reduce expression of the cholesterol-absorption protein NPC1L1 (van der Veen et al., J. Lipid Res. 2005 46: 526-534).

Because there are three subtypes of PPAR and all of them have been shown to play important roles in energy homeostasis and other important biological processes in human body and have been shown to be important molecular targets for treatment of metabolic and other diseases (see Willson, et al. J. Med. Chem. 43: 527-550 (2000)), it is desired in the art to identify compounds which are capable of selectively interacting with only one of the PPAR subtypes or compounds which are capable of interacting with multiple PPAR subtypes. Such compounds would find a wide variety of uses, such as, for example, in the treatment or prevention of obesity, for the treatment or prevention of diabetes, dyslipidemia, metabolic syndrome X and other uses.

SUMMARY OF THE INVENTION

The present invention provides novel salt forms of PPAR modulators which are useful in the treatment or prevention of conditions and disorders including but not limited to those associated with energy homeostasis, lipid metabolism, adipocyte differentiation, inflammation and diabetic conditions, such as, for example, hyperglycemia and hyperinsulinemia. The invention also provides pharmaceutical compositions comprising the salts and methods of their use for the treatment of, for example, conditions and disorders associated with energy homeostasis, lipid metabolism, adipocyte differentiation, inflammation and diabetic conditions, including, but not limited to, hyperglycemia and hyperinsulinemia.

In certain embodiments, salts are formed from a compound of Formula I, which is described in U.S. Patent Application Publications No. US2006/0205736A1, published Sep. 14, 2006, and US2006/0167012A1, published Jul. 27, 2006, the contents of which is hereby incorporated by reference in its entirety. Formula (I) has the following structure:

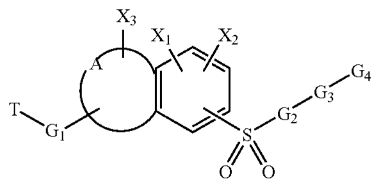

(I)

wherein:

A is a saturated or unsaturated hydrocarbon chain or a heteroatom-comprising hydrocarbon chain having from 3 to 5 atoms, forming a five- to seven-membered ring;

T is selected from the group consisting of —C(O)OH, —C(O)$NH_2$, and tetrazole;

$G_1$, is selected from the group consisting of —$(CR^1R^2)_n$—, —$Z(CR^1R^2)_n$—, $(CR^1R^2)_nZ$—, —$(CR^1R^2)_rZ(CR^1R^2)_s$—;

Z is O, S or NR;

n is 0, 1, or 2;

r and s are 0 or 1;

$R^1$ and $R^2$ are independently selected from the group consisting of hydrogen, halo, optionally substituted lower alkyl, optionally substituted lower heteroalkyl, optionally substituted lower alkoxy, and lower perhaloalkyl or together may form an optionally substituted cycloalkyl;

$X_1$, $X_2$, and $X_3$ are independently selected from the group consisting of hydrogen, optionally substituted lower alkyl, optionally substituted cycloalkyl, halogen, perhaloalkyl, hydroxy, optionally substituted lower alkoxy, nitro, cyano, and $NH_2$;

$G_2$ is selected from the group consisting of a saturated or unsaturated cycloalkyl or heterocycloalkyl linker, optionally substituted with $X_4$ and $X_5$;

$X_4$ and $X_5$ are independently selected from the group consisting of hydrogen, optionally substituted lower alkyl, halogen, lower perhaloalkyl, hydroxy, optionally substituted lower alkoxy, nitro, cyano, $NH_2$, and $CO_2R$;

R is selected from the group consisting of lower alkyl and hydrogen;

$G_3$ is selected from the group consisting of a bond, a double bond, —$(CR^3R^4)_m$—, carbonyl, and —$(CR^3R^4)_m CR^3{=}CR^4$—;

m is 0, 1, or 2;

$R^3$ and $R^4$ are independently selected from the group consisting of hydrogen, optionally substituted lower alkyl, optionally substituted lower alkoxy, optionally substituted aryl, lower perhaloalkyl, cyano, and nitro;

$G_4$ is selected from the group consisting of hydrogen, optionally substituted aryl, optionally substituted heteroaryl, optionally substituted cycloalkyl, optionally substituted heterocycloalkyl, optionally substituted cycloalkenyl, and —$N{=}(CR^5R^6)$; and $R^5$ and $R^6$ are independently selected from the group consisting of hydrogen, optionally substituted aryl, optionally substituted heteroaryl, optionally substituted cycloalkyl, optionally substituted cycloalkenyl, and optionally substituted heterocycloalkyl.

The present invention also provides pharmaceutical compositions comprising one or more salts of the invention and one or more pharmaceutically acceptable diluents, excipients or carriers. The present invention further provides methods for the treatment or prevention: of type II diabetes, hypercholesterolemia, inflammatory disorders or a related disorder, comprising administering to a subject in need of such treatment or prevention a therapeutically effective amount of one or more salts of the invention.

The present invention also provides methods for the treatment or prevention of a condition or disorder mediated by the PPAR receptor, comprising administering to a subject in need of such treatment or prevention a therapeutically effective amount of a salt of the invention.

The novel salt forms of the invention are particularly useful as active pharmaceutical ingredients for the preparation of formulations for use in animals or humans. Thus, the present invention encompasses the use of these solid forms as final drug products. The salts and final drug products of the invention are useful, for example, for the treatment or prevention of conditions and disorders associated with energy homeostasis, lipid metabolism, adipocyte differentiation and inflammation.

DETAILED DESCRIPTION OF THE INVENTION

The present invention discloses salt forms of a compound of Formula I that can modulate at least one peroxisome proliferator-activated receptor (PPAR) function. The compound described herein may be activating both PPARδ and PPARγ or PPARα and PPARδ, or all three PPAR subtypes, or selectively activating predominantly PPARγ, PPARα or PPARδ. Thus, the present invention provides for a method of modulating PPAR comprising contacting said PPAR with a salt of the invention. In certain preferred embodiments, said modulation is selective for PPARδ over PPARα and PPARγ. In certain more preferred embodiments, said modulation of PPARδ is 100-fold selective or greater over said other subtypes. Most preferably, said modulation is 200- to 500-fold selective over said other subtypes.

The present invention relates to a method of modulating at least one peroxisome proliferator-activated receptor (PPAR) function comprising the step of contacting the PPAR with a salt of a compound of Formula I, as described herein. The change in cell phenotype, cell proliferation, activity of the PPAR, expression of the PPAR or binding of the PPAR with a natural binding partner may be monitored. Such methods may be modes of treatment of disease, biological assays, cellular assays, biochemical assays, or the like.

The present invention describes methods of treating disease, comprising administering a therapeutically effective amount of a salt of a compound of Formula I, as described herein, to a patient. Thus, in certain embodiments, the present invention provides methods: for raising HDL, lowering LDLc, shifting LDL particle size from small dense to normal LDL, or inhibiting cholesterol absorption in a subject; for decreasing insulin resistance or lowering blood pressure in a subject; for treating obesity, diabetes, especially Type 2 diabetes, hyperinsulinemia, metabolic syndrome X, dyslipidemia, and hypercholesterolemia; for treating cardiovascular diseases including vascular disease, atherosclerosis, coronary heart disease, cerebrovascular disease, heart failure and peripheral vessel disease in a subject; for treating cancers including colon, skin, and lung cancers in a subject; for treating inflammatory diseases, including rheumatoid arthritis, asthma, osteoarthritis, disorders associated with oxidative stress, inflammatory response to tissue injury, and autoimmune disease in a subject; and for treating polycystic ovary syndrome, climacteric, pathogenesis of emphysema, ischemia-associated organ injury, doxorubicin-induced cardiac injury, drug-induced hepatotoxicity, hypertoxic lung injury, scarring, wound healing, anorexia nervosa and bulimia nervosa in a subject, all comprising the administration of a therapeutic amount of a salt of a compound of Formula I. Preferably, the PPAR may be selected from the group consisting of PPARα, PPARδ, and PPARγ. More preferably, the PPAR is PPARδ.

As used in the present specification the following terms have the meanings indicated:

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)$CH_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20, preferably 2 to 6, carbon atoms. Alkenylene refers to a carbon-carbon double bond system attached at two or more positions such as ethenylene[(—CH═CH—),(—C::C—)]. Examples of suitable alkenyl radicals include ethenyl, propenyl, 2-methylpropenyl, 1,4-butadienyl and the like.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to and including 20, preferably 1 to 10, and more preferably 1 to 6, carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—$CH_2$—).

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20, preferably from 2 to 6, more preferably from 2 to 4, carbon atoms. "Alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(═O)—$NR_2$ group with R as defined herein. The term "N-amido" as used herein, alone or in combination, refers to a RC(═O)NH— group, with R as defined herein. The term "acylamino" as used herein, alone or in combination, embraces an acyl group attached to the parent moiety through an amino group. An example of an "acylamino" group is acetylamino($CH_3$C(O)NH—).

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted.

The term "aryl," as used herein, alone or in combination, means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl(hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$═ derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group-with R and R' as defined herein.

The term "N-carbamyl" as used herein, alone or in combination, refers to a ROC(O)NR'— group, with R and R' as defined herein.

The term "carbonyl," as used herein, when alone includes formyl[-C(O)H] and in combination is a —C(O)— group.

The term "carboxy," as used herein, refers to —C(O)OH or the corresponding "carboxylate" anion, such as is in a carboxylic acid salt. An "O-carboxy" group refers to a RC(O)

O— group, where R is as defined herein. A "C-carboxy" group refers to a —C(O)OR groups where R is as defined herein.

The term "cyano," as used herein, alone or in combination, refers to —CN.

The term "cycloalkyl," as used herein, alone or in combination, refers to a saturated or partially saturated monocyclic, bicyclic or tricyclic alkyl radical wherein each cyclic moiety contains from 3 to 12, preferably five to seven, carbon atom ring members and which may optionally be a benzo fused ring system which is optionally substituted as defined herein. When said cycloalkyl is partially saturated, it may optionally be referred to as cycloalkenyl. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydonapthalene, octahydronapthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—$CF_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —$CH_2$—NH—$OCH_3$.

The terms "heteroaryl" and, interchangeably, "cycloheteroaryl," as used herein, alone or in combination, refers to 3 to 7 membered, preferably 5 to 7 membered, unsaturated heteromonocyclic rings, or fused polycyclic rings in which at least one of the fused rings is unsaturated, wherein at least one atom is selected from the group consisting of O, S, and N. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," or "cycloheteroalkyl," as used herein, alone or in combination, each refer to a saturated, partially unsaturated, or fully unsaturated monocyclic, bicyclic, or tricyclic heterocyclic radical containing at least one, preferably 1 to 4, and more preferably 1 to 2 heteroatoms as ring members, wherein each said heteroatom may be independently selected from the group consisting of nitrogen, oxygen, and sulfur, and wherein there are preferably 3 to 8 ring members in each ring, more preferably 3 to 7 ring members in each ring, and most preferably 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Heterocycle groups of the invention are exemplified by aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of this invention.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in combination, means containing from 1 to and including 6 carbon atoms.

The term "mercaptyl" as used herein, alone or in combination, refers to an RS— group, where R is as defined herein.

The term "nitro," as used herein, alone or in combination, refers to $—NO_2—$

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the $RSO_3—$ group and its anion as the sulfonic acid is used in salt formation.

The term "sulfate" refers to $—HSO_4$.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to $—S(O)_2—$.

The term "N-sulfonamido" refers to a $RS(=O)_2NR'—$ group with R and R' as defined herein.

The term "S-sulfonamido" refers to a $—S(=O)_2NRR'$, group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a $X_3CS(O)_2NR—$ group with X is a halogen and R as defined herein.

The term "trihalomethanesulfonyl" refers to a $X_3CS(O)_2—$ group where X is a halogen.

The term "trihalomethoxy" refers to a $X_3CO—$ group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, arylthio, lower alkylsulfinyl, lower alkylsulfonyl, arylsulfinyl, arylsulfonyl, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, lower carbamate, and lower urea. Two substituents may be joined together to form a fused five-, six-, or seven-menbered carbocyclic or heterocyclic ring consisting of zero to three heteroatoms, for example forming methylenedioxy or ethylenedioxy. An optionally substituted group may be unsubstituted (e.g., $—CH_2CH_3$), fully substituted (e.g., $—CF_2CF_3$), monosubstituted (e.g., $—CH_2CH_2F$) or substituted at a level anywhere in-between fully substituted and monosubstituted (e.g., $—CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and $R^n$ where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and 1-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

In the event that $G_3$ is designated to be "a bond", the structure shown below (right side) is intended: the entity designated $G_3$ collapses to a single bond connecting $G_2$ and $G_4$:

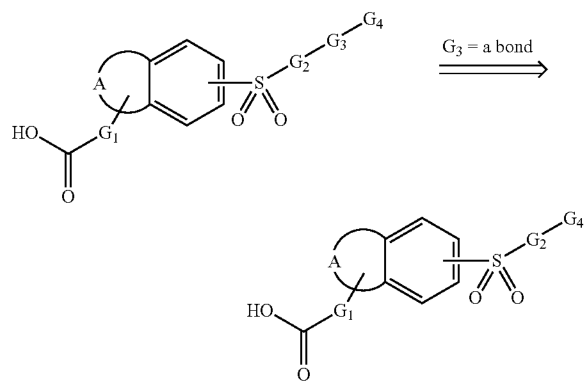

Similarly, when, within $G_1$, n is 0 or both r and s are 0, $G_1$ collapses to a bond connecting A and T.

As used herein, "diabetes" refers to type I diabetes mellitus (juvenile diabetes) or type II diabetes mellitus (non-insulin-dependent diabetes mellitus or NIDDM), preferably, type II diabetes mellitus.

As used herein, the term "PPAR-mediated condition or disorder" or "PPAR-mediated condition or disease" and the like refers to a condition, disorder, or disease characterized by inappropriate, e.g. less than or greater than normal, PPAR activity. Inappropriate PPAR activity might arise as the result of PPAR expression in cells which normally do not express PPAR, increased PPAR expression (leading to, e.g. certain energy homeostasis, lipid metabolism, adipocyte differentiation and inflammatory disorders and diseases), or, decreased PPAR expression (leading to, e.g. certain energy homeostasis, lipid metabolism, adipocyte differentiation and inflammatory disorders and diseases). A PPAR mediated condition or disorder may be completely or partially mediated by inappropriate PPAR activity. However, a PPAR-mediated condition or disorder is one in which modulation of PPAR results in some effect on the underlying condition or disease (e.g. a PPAR modulator results in some improvement in patient well-being in at least some patients). Exemplary PPAR-mediated conditions and disorders include, but are not limited to, metabolic disorders, e.g., diabetes, type II diabetes, obesity, hyperglycemia, insulin resistance, hyperinsulinemia, hypercholesterolemia, hypertension, hyperlipoproteinemia, hyperlipidemia, hypertriglylceridemia and dyslipidemia, and inflammatory conditions, e.g. rheumatoid arthritis and atherosclerosis.

The term "modulate," in its various forms, refers to the ability of a compound to increase or decrease the function or activity associated with a particular peroxisome proliferator-activated receptor, preferably the PPARδ receptor. Modulation, as described herein, includes the inhibition or activation of PPAR, either directly or indirectly. Inhibitors are compounds that, e.g., bind to, partially or totally block stimulation, decrease, prevent, delay activation, inactivate, desensitize, or down regulate signal transduction, e.g., antagonists. Activators are compounds that, e.g., bind to, stimulate, increase, open, activate, facilitate, enhance activation, sensitize or up regulate signal transduction, e.g., agonists. Further, modulation of PPAR receptor activity is intended to encompass antagonism, agonism, partial antagonism and/or partial agonism of the activity associated with the PPAR receptor.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant the diluent, excipient or carrier must be compatible with the other ingredients of the formulation and not deleterious to the recipient thereof.

The term "therapeutically effective amount" refers to the amount of the subject salt that will elicit the biological or medical response of a tissue, system, animal or human that is being sought by the researcher, veterinarian, medical doctor or other clinician or that is sufficient to prevent development of or alleviate to some extent one or more of the symptoms of the disease being treated. In reference to the treatment of diabetes or dyslipidemia a therapeutically effective amount may refer to that amount which has the effect of (1) reducing the blood glucose levels; (2) normalizing lipids, e.g. triglycerides, low-density lipoprotein; (3) relieving to some extent (or, preferably, eliminating) one or more symptoms associated with the disease, condition or disorder to be treated; and/or (4) raising HDL.

The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition (including, but not limited to, metabolic disorders), previous therapy, the patient's health status and response to the drugs, and the judgment of the treating physician. It is considered well within the skill of the art for one to determine such enhancing-effective amounts by routine experimentation.

The term "salt" is meant to include those salts prepared by combining the compounds of Formula I with both acidic and basic reagents. The present invention includes compounds listed above in the form of salts, in particular acid addition salts. Suitable salts include those formed with both organic and inorganic acids. Acid addition salts can be obtained by contacting the neutral form of such compounds with a sufficient amount of the desired acid, either neat or in a suitable inert solvent. Such acid addition salts will normally be pharmaceutically acceptable. However, salts of non-pharmaceutically acceptable salts may be of utility in the preparation and purification of the compound in question. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic; propionic; isobutyric; maleic; malonic; benzoic; succinic; suberic; fumaric; mandelic; phthalic; benzenesulfonic; toluenesulfonic, including p-toluenesulfonic, m-toluenesulfonic, and o-toluenesulfonic; citric; tartaric; methanesulfonic; and the like. Also included are salts of amino acids such as arginate and the like, and salts of organic acids like glucuronic or galactunoric acids and the like (see, for example, Berge et al. J. Pharm. Sci. 66:1-19 (1977)). Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Particular salts described below include "tosylate salts" or "p-toluenesulfonate salts" of the compounds of Formula I of the invention. A tosylate or p-toluenesulfonate salt is an acid addition salt formed from p-toluenesulfonic acid.

The terms, "polymorphs" and "polymorphic forms" and related terms herein refer to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice. The differences in physical properties exhibited by polymorphs affect pharmaceutical parameters such as storage stability, compressibility and density (important in formulation and product manufacturing), and dissolution rates (an important factor in bioavailability). Differences in stability can result from changes in chemical reactivity (e.g. differential oxidation, such that a dosage form discolors more rapidly when comprised of one polymorph than when comprised of another polymorph) or mechanical changes (e.g. tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing, for example, one polymorph might be more likely to form solvates or might be difficult to filter and wash free of impurities (i.e., particle shape and size distribution might be different between polymorphs).

Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation.

Techniques for characterizing polymorphs include, but are not limited to, differential scanning calorimetry (DSC), X-ray powder diffractometry (XRPD), single crystal X-ray diffractometry, vibrational spectroscopy, e.g. IR and Raman spectroscopy, solid state NMR, hot stage optical microscopy, scanning electron microscopy (SEM), electron crystallography and quantitative analysis, particle size analysis (PSA), surface area analysis, solubility studies and dissolution studies.

The term, "solvate," as used herein, refers to a crystal form of a substance which contains solvent.

The term "hydrate" refers to a solvate wherein the solvent is water.

The term, "desolvated solvate," as used herein, refers to a crystal form of a substance which can only be made by removing the solvent from a solvate.

The term, "amorphous form," as used herein, refers to a noncrystalline form of a substance.

In addition to salt, the invention comprehends compounds which are in a prodrug form. The term "prod rug" refers to a compound that is made more active in vivo. Certain compounds of the present invention may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prod rug. An example, without limitation, of a prodrug would be a compound which is administered as an ester (the "prod rug"), but then is metabolically hydrolyzed to the carboxylic acid, the active entity. Additional examples include peptidyl derivatives of a compound.

The present invention is directed to salts of the compounds of Formula I, compositions comprising the salts alone or in combination with other active ingredients, methods of their use in the modulation of receptor activity, particularly PPAR activity. While not intending to be bound by any particular theory of operation, the stability and other properties of the salts are beneficial for manufacturing, formulation and bioavailability of the PPAR modulator.

In another aspect, the present invention relates to a method of treating a disease comprising identifying a patient in need thereof, and administering a therapeutically effective amount of a salt of a compound of Formula I, as described herein, to the patient.

The salts of the invention are useful in the treatment of a disease or condition ameliorated by the modulation of a PPAR-delta. Specific diseases and conditions modulated by PPAR-delta and for which the compounds and compositions are useful include but are not limited to dyslipidemia, syndrome X, heart failure, hypercholesteremia, cardiovascular disease, type II diabetes mellitus, type 1 diabetes, insulin resistance hyperlipidemia, obesity, anorexia bulimia, inflammation and anorexia nervosa. Other indications include reduction of scarring and wound healing.

The salts of the invention may also be used (a) for raising HDL in a subject; (b) for treating Type 2 diabetes, decreasing insulin resistance, treating obesity, or lowering blood pressure in a subject; (c) for decreasing LDLc in a subject; (d) for shifting LDL particle size from small dense to normal dense LDL in a subject; (e) for reducing cholesterol absorption or increasing cholesterol excretion in a subject; (f) for reducing the expression of NPC1L1 in a subject; (g) for treating atherosclerotic diseases including vascular disease, coronary heart disease, cerebrovascular disease and peripheral vessel disease in a subject; or (h) for treating inflammatory diseases, including asthma, rheumatoid arthritis, osteoarthritis, disorders associated with oxidative stress, inflammatory response to tissue injury, psoriasis, ulcerative colitis, dermatitis, and autoimmune disease in a subject.

The salts of the invention may also be used for treating, ameliorating, or preventing a disease or condition selected from the group consisting of obesity, diabetes, hyperinsulinemia, metabolic syndrome X, polycystic ovary syndrome, climacteric, disorders associated with oxidative stress, inflammatory response to tissue injury, pathogenesis of emphysema, ischemia-associated organ injury, doxorubicin-induced cardiac injury, drug-induced hepatotoxicity, atherosclerosis, and hypertoxic lung injury.

The compositions containing the salts described herein can be administered for prophylactic and/or therapeutic treatments. In therapeutic applications, the compositions comprising these salts are administered to a patient already suffering from a disease, condition or disorder mediated, modulated or involving the PPARs, including but not limited to metabolic diseases, conditions, or disorders, as described above, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

In prophylactic applications, compositions containing the salts described herein are administered to a patient susceptible to or otherwise at risk of a particular disease, disorder or condition mediated, modulated or involving the PPARs, including but not limited to metabolic diseases, conditions, or disorders, as described above. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial).

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. When the symptoms have been alleviated to the desired level, treatment can cease. Patients can, however, require intermittent treatment on a long-term basis upon any recurrence of symptoms.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, preferably 1-1500 mg per day. The desired dose may conveniently be presented in a single dose or as divided doses administered at appropriate intervals, for example as two, three, four or more sub-doses per day.

In certain instances, it may be appropriate to administer at least one of the salts described herein in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the salts described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of the salts of the compound of formula (I) with: (a) statin and/or other lipid lowering drugs for example MTP inhibitors and LDLR upregulators; (b) antidiabetic agents, e.g. metformin, sulfonylureas, or PPAR-gamma, PPAR-alpha and PPAR-alpha/gamma modulators (for example thiazolidinediones such as e.g. Pioglitazone and Rosiglitazone); and (c) antihypertensive agents such as angiotensin antagonists, e.g., telmisartan, calcium channel antagonists, e.g. lacidipine and ACE inhibitors, e.g., enalapril.

In any case, the multiple therapeutic agents (one of which is one of the compounds described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks.

Suitable routes of administration may, for example, include oral, rectal, transmucosal, pulmonary, ophthalmic or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer a salt of the present invention in a local rather than systemic manner, for example, via injection of the compound directly into an organ, often in a depot or sustained release formulation. Furthermore, one may administer the drug in a targeted drug delivery system, for example, in a liposome coated with organ-specific antibody. The liposomes will be targeted to and taken up selectively by the organ.

The pharmaceutical compositions of the salts of the present invention may be manufactured in a manner that is itself known, e.g., by means of conventional mixing, dissolving, granulating, dragee-making, levigating, emulsifying, encapsulating, entrapping or compression processes.

Pharmaceutical compositions for use in accordance with the present invention thus may be formulated in conventional manner using one or more physiologically acceptable carriers comprising excipients and auxiliaries which facilitate processing of the salts into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

For intravenous injections, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art. For other parenteral injections, the agents of the invention may be formulated in aqueous or nonaqueous solutions, preferably with physiologically compatible buffers or excipients. Such excipients are generally known in the art.

For oral administration, the compositions can be formulated readily by combining the salts with pharmaceutically acceptable carriers or excipients well known in the art. Such carriers enable the salts of the invention to be formulated as tablets, powders, pills, dragees, capsules, liquids, gels, syrups, elixirs, slurries, suspensions and the like, for oral ingestion by a patient to be treated. Pharmaceutical preparations for oral use can be obtained by mixing one or more solid excipient with one or more salt of the invention, optionally grinding the resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethyl cellulose; or others such as: polyvinylpyrrolidone (PVP or povidone) or calcium phosphate. If desired, disintegrating agents may be added, such as the cross-linked croscarmellose sodium, polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal or sublingual administration, the compositions may take the form of tablets, lozenges, or gels formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the salts may also be formulated as a depot preparation. Such long acting formulations may be administered by implantation (for example subcutaneously or intramuscularly) or by intramuscular injection. Thus, for example, the salts may be formulated with suitable polymeric or hydrophobic materials (for example as an emulsion in an acceptable oil) or ion exchange resins, or as sparingly soluble derivatives, for example, as a sparingly soluble salt.

Many delivery systems for hydrophobic pharmaceutical salts may be employed. Liposomes and emulsions are well known examples of delivery vehicles or carriers for hydrophobic drugs. Certain organic solvents such as N-methylpyrrolidone also may be employed, although usually at the cost of greater toxicity. Additionally, the salts may be delivered using a sustained-release system, such as semipermeable matrices of solid hydrophobic polymers containing the therapeutic agent. Various sustained-release materials have been established and are well known by those skilled in the art.

Sustained-release capsules may, depending on their chemical nature, release the salts for a few weeks up to over 100 days. Depending on the chemical nature and the biological stability of the therapeutic reagent, additional strategies for protein stabilization may be employed.

The present invention provides particular pharmaceutically acceptable salts of compounds of Formula I, potent modulators of PPAR and in particular the PPARδ receptor, having particular utility for the treatment or prevention of conditions and disorders associated with energy homeostasis, lipid metabolism, adipocyte differentiation, inflammation, and diabetes or diabetic conditions. This aspect of the invention provides salts of the compounds of Formula I including but not limited to sulfate, sodium, potassium, magnesium, calcium, hydrochloride, phosphate, and p-toluenesulfonate salts.

In certain embodiments, the present invention provides the p-toluenesulfonic acid (tosylate) salt of Compound 1.

In the p-toluenesulfonate salt forms of the compounds of Formula I, p-toluenenesulfonic acid is according to Formula (II):

(II)

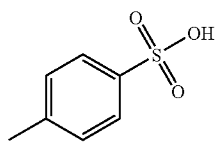

Each salt of the invention can be made from a preparation of a compound of Formula I. The compounds of Formula I can be synthesized or obtained according to any method apparent to those of skill in the art. In preferred embodiments, compounds of Formula I are prepared according to the methods described in detail in U.S. patent application Ser. No. 60/079,813, the contents of which is hereby incorporated by reference in its entirety. The compounds of Formula I prepared by any method can be contacted with an appropriate acid, either neat or in a suitable inert solvent, to yield the salt forms of the invention.

For example, compounds of Formula 1 can be contacted with p-toluenesulfonic acid to yield the p-toluenesulfonate (tosylate) salt form of the invention. Compounds of Formula 1, including Compound 1 and Compound 2 below, their racemates, and racemic mixtures thereof, prepared by any method can be contacted with a reagent selected from the group consisting of calcium acetate, hydrochloric acid, phosphoric acid, sulfuric acid, sodium hydroxide, potassium hydroxide, magnesium acetate, and p-toluenesulfonic acid, preferably in a 1:1 ratio, in a suitable solvent. Such solvents include but are not limited to diisopropyl ether, toluene, dichloromethane, and acetonitrile. Any technique known in the art can be used to vary conditions to induce precipitation or crystallization, including, without limitation: stirring for varying lengths of time at varying ambient conditions, the addition of hexanes or diethyl ether, evaporation, and reduction of temperature. In particular, 4-[cis-2,6-dimethyl-4-(4-trifluoromethoxy-phenyl)-piperazine-1-sulfonyl]-indan-2-carboxylic acid can be contacted with p-toluenesulfonic acid to yield 4-[cis-2,6-dimethyl-4-(4-trifluoromethoxy-phenyl)-piperazine-1-sulfonyl]-indan-2-carboxylic acid tosylate. The present invention provides for salts of each racemate of compounds of Formula 1, including (S)-4-[cis-2,6-dimethyl-4-(4-trifluoromethoxy-phenyl)-piperazine-1-sulfonyl]-indan-2-carboxylic acid tosylate (Compound 1 tosylate).

Other salts of compounds of Formula 1 may be formed. In particular, the present invention provides for salts of 4-[cis-2,6-Dimethyl-4-(4-trifluoromethoxy-benzyl)-piperazine-1-sulfonyl]-indan-2-carboxylic acid and each of its isolated racemates.

As shown in detail in the examples below, the tosylate salt of the compounds of Formula I display excellent crystallization properties amongst the various salts of the compounds of Formula I.

In another aspect, the present invention provides pharmaceutical compositions for modulating PPARδ activity in humans and animals.

All references, patents or applications, U.S. or foreign, cited in the application are hereby incorporated by reference as if written herein.

EXAMPLE 1

Synthesis of Compound 1

(I)

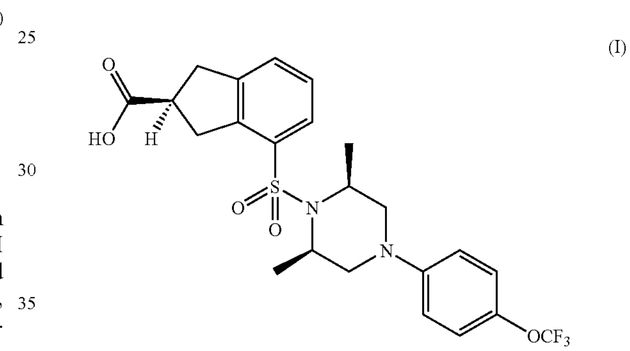

(S)-4-[cis-2,6-Dimethyl-4-(4-trifluoromethoxy-phenyl)-piperazine-1-sulfonyl]-indan-2-carboxylic acid Step 1

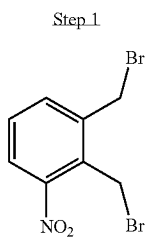

1,2-Bis(bromomethyl)-3-nitrobenzene: A 5 liter flask was charged with 20 g 1,2-dimethyl-3-nitrobenzene (0.13 mol), 50 g N-bromosuccinimide (0.28 mol), 5 g azobis(isobutyronitrile)(3.0 mmol), and 200 mL of dichloromethane. This was irradiated with a 120 watt floodlamp to effect gentle relux under nitrogen for 18 hours. The mixture was then cooled and precipitated succinimide was removed by filtration. The filtrate was concentrated and the residue was purified by chromatography on silica (5%-50% $CH_2Cl_2$ in hexanes) to give 2.6 g white solid (64%).

Step 2

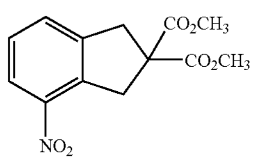

Dimethyl-4-nitroindane-2,2-dicarboxylate: To a solution stirred under nitrogen at room temperature of 5.0 mL methanol in 15.0 mL ether was added 0.84 g 60% sodium hydride (0.021 mol) in small portions (sodium hydride was used because metallic sodium was not available). After the addition was complete, the nearly clear and colorless solution was stirred for 5 minutes. To it was then added 1.3 g dimethyl malonate, giving a slightly cloudy colorless solution. To this was rapidly added a suspension of 3.1 g 1,2-bis(bromomethyl)3-nitrobenzene, which immediate gave a precipitate suspended in a dark green solution. This was removed by filtation and the filtrate was concentrated. The residue was purified on silica (20%-100% $CH_2Cl_2$ in hexanes) to give 1.93 g off-white solid (67%).

Step 3

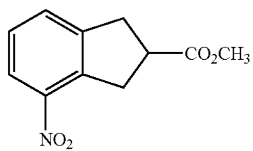

Methyl-4-nitroindane-2-carboxylate: A mixture of 4.84 g dimethyl-4-nitroindane-2,2-dicarboxylate (0.0167 mol), 0.84 g lithium chloride (0.0198 mol), 1.1 mL water, and 18 mL dimethylsulfoxide was heated to 160 C under nitrogen for two hours. It was then allowed to cool and the dimethylsulfoxide was removed under high vacuum. The residue was purified on silica (10%-100% $CH_2Cl_2$ in hexanes) to give 2.5 g white solid (65%).

Step 4

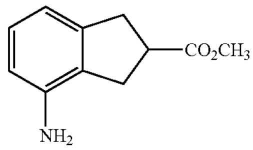

Methyl-4-aminoindane-2-carboxylate: A mixture of 2.4 g methyl-4-nitroindane-2-carboxylate (0.11 mol), 1.1 g 10% palladium on carbon (0.01 mol), and 15 mL ethyl acetate was shaken under 55 PSI hydrogen for 1 hour. It was then filtered and the filtrate was concentrated to give 2.07 g white solid (100%).

Step 5

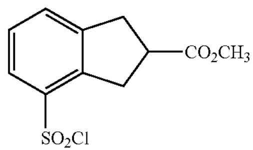

Methyl-4-chlorosulfonyl-2-carboxylate: A mixture of 2.5 g methyl-4-aminoindane-2-carboxylate (0.013 mol), 12.5 mL acetonitrile, and 12.5 mL $H_2O$ was cooled to −5 C in an ice-salt bath. To this was added 2.6 mL concentrated HCl (0.014 mol). To this was added dropwise over 20 minutes a solution of 1.0 g sodium nitrite (0.021 mol) in 5 mL water. After the addition was complete the solution was stirred for 20 minutes. It was then transferred to a jacketed addition funnel cooled with ice water. The solution was added dropwise to a solution stirred under nitrogen at 55 C of 4.2 g potassium thioxanthate (0.026 mol) in 20 mL $H_2O$. As the addition took place, a dark layer rose to the top of the diazonium ion solution which was not added. After the addition was complete the mixture was stirred at 55 C for 30 minutes, then was allowed to cool and was extracted with 40 mL ethyl acetate. The organic layer was dried ($MgSO_4$) and concentrated. The residue was loaded on 80 mL silica gel which was slurry-packed in hexanes. This was eluted with 100 mL hexanes, then 1%-50% $CH_2Cl_2$ in hexanes in 50 mL fractions to give 1.3 g amber oil (33%).

A mixture of 3.6 g of the above compound in 30 mL $CCl_4$ and 10 mL $H_2O$ was vigorously stirred and cooled to 3 C. Chlorine gas was bubbled through at such a rate that the temperature stayed below 10 C. After conversion was complete, the phases were separated and the aqueous layer was extracted with $CH_2Cl_2$. The combined organic layers were dried ($MgSO_4$) and concentrated to give 4.0 g yellow oil (>100%).

Step 6

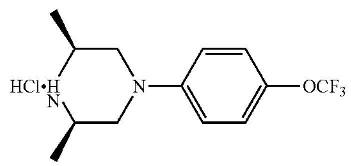

4-[cis-2,6-Dimethyl-4-(4-trifluoromethoxy-phenyl)-piperazine hydrochloride: A mixture of 200 g cis-2,6-dimethylpiperazine (1.75 mol), 421 g 1-bromo-4-trifluoromethoxy-bezene (1.74 mol), 200 g sodium-t-butoxide (2.08 mol), 10 g tris(dibenzylideneacetone)dipalladium (0.011 mol), 20 g 1,3-bis(2,6-diisopropylphenyl) imidazolium chloride (0.047 mol), and 4 L toluene was degassed through 5 vacuum-nitrogen cycles (Firestone valve) and heated to 100 C under nitrogen for 2 hours. The reaction was allowed to cool and was filtered through celite. The filtrate was concentrated under vacuum and the residue was diluted with hexanes (2 L). The mixture was filtered and the filtrate diluted with diethyl ether (2 L). To this was added concentrated HCl (150 ml, 1.8 mol) and the resulting mixture agitated briefly resulting in precipitation of the product which was collected by filtration and dried under vacuum (2 mm Hg, 14 hr) to give 467 g tan solid (86%).

Step 7

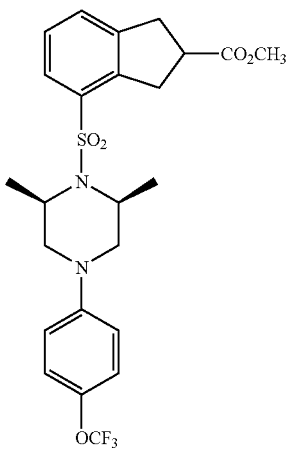

4-[cis-2,6-Dimethyl-4-(4-trifluoromethoxy-phenyl)-piperazine-1-sulfonyl]-indan-2-methyl ester: A mixture of 2.13 g methyl-4-chlorosulfonyl-2-carboxylate (0.0078 mol), 3.0 g 4-[cis-2,6-dimethyl-4-(4-trifluoromethoxy-phenyl)-piperazine hydrochloride (0.0109 mol), 20 mL acetonitrile, and 3.0 g $K_2CO_3$ (0.0217 mol) was heated to 60 C under nitrogen with stirring for 20 hours. It was then filtered and the filtrate was concentrated. The residue was purified by chromatography on silica (5%-50% EtOAc in hexanes) to give 2.64 g viscous yellow oil (66%).

Step 8

4-[cis-2,6-Dimethyl-4-(4-trifluoromethoxy-phenyl)-piperazine-1-sulfonyl]-indan-2-carboxylic acid: To a solution stirred at room temperature of 2.64 g 4-[cis-2,6-dimethyl-4-(4-trifluoromethoxy-phenyl)-piperazine-1-sulfonyl]-indan-2-methyl ester (0.0052 mol) in the minimum amount of THF (ca 15 mL) was added a solution of 0.14 g LiOH (0.0057 mol) in the minimum amount of water (ca 2.5 mL). This was capped and stirred at room temperature for 12 hours. Examination by HPLC showed the reaction was 85% complete so an additional 0.020 g LiOH (0.125 eq total) was added and stirring was continued for 3 hours. It was then concentrated to remove THF and partitioned between EtOAc and water. The aqueous layer was treated with 0.54 mL conc. HCl. It was then extracted with ethyl acetate. The organic layer was dried ($MgSO_4$) and concentrated to give 2.38 g yellow amorphous solid (93%).

Step 9

(S)-4-[cis-2,6-Dimethyl-4-(4-trifluoromethoxy-phenyl)-piperazine-1-sulfonyl]-indan-2-carboxylic acid: The compound (S)-4-[cis-2,6-dimethyl-4-(4-trifluoromethoxy-phenyl)-piperazine-1-sulfonyl]-indan-2-carboxylic acid was obtained by chiral HPLC (chiralpak ASH 0.46×15 cm Hex/IPA 94:6 (v/v) with 0.1% TFA, flow rate 1 ml/min) separation from the racemate. LCMS 497.1 $(M-1)^-$.

EXAMPLE 2

Synthesis of Compound 2

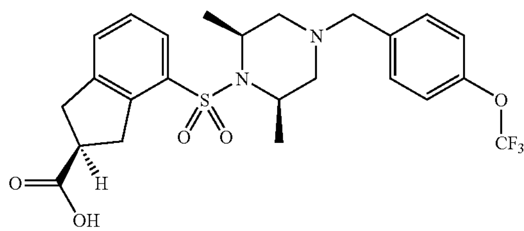

(S)-4-[cis-2,6-Dimethyl-4-(4-trifluoromethoxy-benzyl)-piperazine-1-sulfonyl]-indan-2-carboxylic acid Step 1

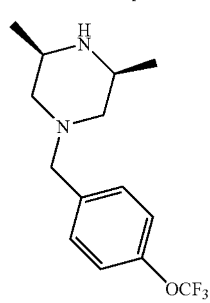

cis-3,5-Dimethyl-1-(4-trifluoromethoxy-benzyl)-piperazine: To a solution of 4-(trifluoromethoxy)-benzaldehyde (776 uL, 4.38 mmol) in methylene chloride (30 mL) was added cis-2,6-dimethyl piperazine (1.0 g, 8.77 mmol). After 1 hour sodium triacetoxy borohydride (2.45 g, 8.77 mmol) was added to the mixture. The solution was stirred at room temperature for an additional 4 hours. The reaction was concentrated in vacuo, diluted with ethyl acetate and extracted with 1N HCl (2×50 mL). The aqueous layer was then neutralized with NaOH and extracted with ethyl acetate (3×50 mL). The organic layer was dried ($Na_2SO_4$) and concentrated to provide cis-3,5-dimethyl-1-(4-trifluoromethoxy-benzyl)-piperazine (1.01 g, 80%). $^1H$ NMR (400 MHz, $CD_3OD$) δ 7.42 (d, 2H), 7.23 (d, 2H), 3.54 (s, 2H), 2.98-2.88 (m, 2H), 2.82-2.74 (m, 2H), 1.69 (t, 2H), 1.05 (d, 6H); LCMS 289.5 $(M+1)^+$.

Step 2

4-[cis-2,6-Dimethyl-4-(4-trifluoromethoxy-benzyl)-piperazine-1-sulfonyl]-indan-2-carboxylic acid: The compound 4-[cis-2,6-dimethyl-4-(4-trifluoromethoxyl-benzyl)-piperazine-1-sulfonyl]-indan-2-carboxylic acid was synthesized according to the procedure in Example 1 using cis-3,5-dimethyl-1-(4-trifluoromethoxy-benzyl)-piperazine. $^1H$ NMR (400 MHz, $CD_3OD$) δ 7.74-7.64 (m, 4H), 7.47 (d, 1H), 7.39-7.28 (m, 2H), 4.42 (s, 2H), 4.21-2.18 (m, 2H), 3.50-3.34 (m, 5H), 3.33-3.19 (m, 4H), 1.56 (d, 6H); LCMS 497.5 $(M+1)^+$.

Step 3

(S)-4-[cis-2,6-Dimethyl-4-(4-trifluoromethoxy-benzyl)-piperazine-1-sulfonyl]-indan-2-carboxylic acid: A single enantiomer of Example 2 was obtained with the following protocol. The product from example 2 Step 1 and the product from Example 1 Step 5 were reacted using the conditions outlined in Example 9 Step 6 to yield the racemic methyl ester. Chiral separation using OJ-H, 25% methanol in $CO_2$ (100 bar), 5 mL/min followed by hydrolysis using conditions outlined in Example 1 Step 7 provided (S)-4-(cis-2,6-dimethyl-4-(3-trifluoromethoxy)benzyl)piperazin-1-ylsulfonyl)-2,3-dihydro-1H-indene-2-carboxylic acid. $^1H$ NMR (400 MHz, $CD_3OD$) δ 7.66 (d, 1H), 7.46 (d, 1H), 7.41 (d, 2H), 7.36-7.30 (m, 1H), 7.19 (d, 2H), 4.08-3.99 (m, 1H), 3.94-3.8 (m, 1H), 3.56-3.49 (m, 2H), 3.43 (s, 2H), 3.40-3.22 (m, 3H), 2.57 (t, 2H), 2.09-1.92 (m, 2H), 1.56 (d, 6H); LCMS 513.5

EXAMPLE 3

Preparation of Salts of Compound 1

Benzathine:

Compound 1 and benzathine base combined in 1:1 molar ratio in DCM solvent; no precipitation. Allowed to evaporate, yielding a clear film. Placed in vacuum oven 1 day, resulting in a tacky light yellow film.

Calcium:

Compound 1 and base ($Ca(OAc)_2$) were combined in 1:1 molar ratio in methanol solvent. No precipitation occurred, so the solution was allowed to evaporate. White solids and broken glass formed upon drying. Ether solvent was added; most of the solid dissolved, so the solution was placed in a freezer for 1 day, resulting in a clear solution with few solids. This solution was left to evaporate under ambient conditions, yielding solids with areas of birefringence.

Hydrochloride:

Compound 1 and hydrochloric acid were combined in 1:1 molar ratio in methanol. No precipitation occurred, so the solution was allowed to evaporate yielding a clear oil upon drying. This oil was dissolved in DCM and hexanes were added, yielding a white solution which was then capped and left under ambient conditions for one day. A clear solution resulted which was placed in a freezer.

Phosphate:

Compound 1 and phosphoric acid were combined in 1:1 molar ratio in acetonitrile (ACN) solvent. No precipitation occurred. Tetrahydrofuran (THF) antisolvent was added, still resulting in no precipitation. The solution was allowed to evaporate under ambient conditions, yielding an opaque film. This was placed in an ambient vacuum oven for 1 day. White solids were recovered.

Sulfate:

Compound 1 and sulfuric acid were combined in a 1:1 molar ratio in methanol solvent. No precipitation occurred, so the solution was allowed to evaporate, yielding a clear film. This was placed in an ambient vacuum oven for 3 days, resulting in a clear film with brown streaks throughout.

Potassium:

Compound 1 and KOH base were combined in a 1:1 molar ratio in ethanol solvent. Hexanes were added. No precipitation occurred, so the solution was allowed to evaporate, resulting in a light yellow film. This was redissolved in EtOH, and an attempt was made at precipitation by adding hexanes, resulting in a foggy solution, which was subsequently filtered. No solid was recovered upon filtration; the filtrate was allowed to evaporate, yielding a clear film. This was dissolved in ACN and left to evaporate to half volume in order to concentrate the solution. Ethyl ether was added, resulting in no precipitation. The solution was allowed to evaporate, yielding a clear film. This was left to evaporate under ambient conditions for three days, yielding light yellow solids.

Magnesium:

Compound 1 and magnesium acetate were combined in a 1:1 molar ratio in methanol solvent. No precipitation occurred, so the solution was allowed to evaporate, resulting in a clear oil with a milky film. Ethyl ether was added, and the clear oil dissolved while the milky film coagulated at bottom of the reaction vessel into small drops. The solution was placed in a freezer for one day, yielding a clear solution with immiscible oil drops. This was left to evaporate under ambient conditions, leaving a clear film. This was placed in an ambient vacuum oven for one day, yielding off white solids.

Sodium:

Compound 1 and sodium hydroxide were combined in a 1:1 molar ratio in ethanol solvent. Hexanes were added; no precipitation occurred, so the solution was allowed to evaporate, resulting in a light yellow film. This was dissolved in MeOH, and an attempt at precipitation was made by adding ethyl ether. No precipitation occurred, so the solution was allowed to evaporate, yielding a clear film. This was dissolved in dichloromethane (DCM) and left to evaporate to half volume in order to concentrate the solution. The addition of hexanes resulted in a white precipitate which was placed on an ambient slurry wheel for four days, resulting in a clear, immiscible oil in solution. This was stirred under ambient conditions with a magnetic stirbar for two days, resulting in a clear oil at the base of the solution. This was left to evaporate under ambient conditions, yielding a clear film. This was placed in an ambient vacuum oven for one day, yielding off white solids.

P-Toluenesulfonate:

Compound 1 and p-toluenesulfonic acid were combined in a 1:1 molar ratio in tetrahydrofuran (THF) solvent. No precipitation occurred. The clear solution was chilled in an ice water bath and allowed to evaporate under a dry nitrogen purge, yielding off-white solids.

EXAMPLE 4

Alternate Direct Preparation of the Tosylate Salt of Compound 1

Step 1

32% HCI is added to a solution of sodium nitrite in water and acetonitrile at 0° C. The solution is cooled to −5° C. and a solution of (R,S)-4-amino-indan-2-carboxylic acid methyl ester hydrochloride in water, acetonitrile, and 32% HCl is added, keeping the temperature between −7 and −10° C. The resulting cold diazonium solution is added to a solution of potassium ethyixanthogenate, in water and acetonitrile, at 60° C. After heating at 60° C., the mixture is cooled to room temperature and extracted from dichioromethane. The organic solution is charged into the reactor and concentrated under reduced pressure. Dichloromethane and water are added, the mixture cooled to 5° C., and chlorine gas passed through the mixture. The organic solution is separated and the aqueous solution is extracted from dichioromethane. The combined organic solution is dried over magnesium sulfate and concentrated under reduced pressure to afford (R,S)-4-chlorosulfonyl-indan-2-carboxylic acid. HPLC may be used to monitor the reaction.

Step 2:

Potassium carbonate is added to a mixture of cis-3,5-dimethyl-1-(4-trifluoromethoxy-phenyl)-piperazine hydrochloride in dichioromethane and water. After stirring at room temperature, the organic phase is collected and the aqueous layer extracted from dichioromethane. The combined organic solution is charged into the reactor and concentrated under reduced pressure, followed by the addition of acetonitrile and potassium carbonate. A solution of (R,S)-4-chlorosulfonyl-indan-2-carboxylic acid, in acetonitrile, is added to the reaction mixture. After heating at 50° C., the reaction mixture is cooled to 20° C. The mixture is transferred into a 200 L movable agitation feed tank, which is charged with Celite, and the suspension is stirred. The suspension is filtered, filter cake washed with acetonitrile, and the filtrate is concentrated under reduced pressure, cooled to 0-5° C., and 32% HCl added. Following further concentration and filtration, the filtrate is concentrated to give an oil which is purified by silica gel chromatography and recrystallized from isopropanol to give the product (R,S)-4-[cis-2,6-dimethyl-4-(4-trifluoromethoxy-phenyl)-piperazine-1-sulfonyl]-indan-2-carboxylic acid methyl ester (>95% by HPLC).

Step 3:

Simulated moving bed (SMB) chromatography was used to separate the S- and R-enantiomers of (R,S)-4-[cis-2,6-dimethyl-4-(4-trifluoromethoxy-phenyl)-piperazine-1-sulfonyl]-indan-2-carboxylic acid methyl ester. The SMB method uses a Chiralpak AS column and nheptane/isopropanol (1:1 v/v) to yield the S-enantiomer, (S)-4-[cis-2,6-dimethyl-4-(4-trifluoromethoxy-phenyl)-piperazine-1-sulfonyl]-indan-2-carboxylic acid methyl ester (>99.0% by chiral HPLC).

Step 4:

To a solution of (S)-4-[cis-2,6-dimethyl-4-(4-trifluoromethoxy-phenyl)-piperazine-1-sulfonyl]-indan-2-carboxylic acid methyl ester, in THF, is added a solution of lithium hydroxide in water, which is stirred at 20° C. and concentrated under reduced pressure. The reaction mixture is cooled to 9° C., neutralized with 32% HCl, and extracted from toluene. Water is removed from the organic solution by azeotropic distillation. Following distillation, the organic solution is cooled to ambient temperature and transferred to a feeding vessel. The reactor is charged with p-toluenesulfonic acid in toluene and water is removed by azeotropic distillation. The solution is cooled to 60° C., followed by the addition of the organic solution from the feeding vessel. The mixture is stirred at 83° C., then cooled to 10° C. to induce crystallization. The product suspension is filtered, the filter cake rinsed with heptane, and dried on a rotovap, at 40° C., to afford (S)-4-[cis-2,6-dimethyl-4-(4-trifluoromethoxy-phenyl)-piperazine-1-sulfonyl]-indan-2-carboxylic acid tosylate. $^{1}$HNMR δ 1.60 (d), 1.62 (d), 2.33 (s), 3.23 (m), 3.49 (m), 3.39 (m), 4.05 (m), 4.49 (m), 3.40 (dd), 3.23 (dd), 7.14 (d), 7.14 (d), 7.09 (d), 7.09 (d), 7.59 (d), 7.59 (d), 7.71 (d), 7.26, dd, 7.57 (d), 7.57 (d), 7.40 (d).

XRPD Characterization of the Tosylate Salt of Compound 1

The methyl ester precursor of (S)-4-[cis-2,6-dimethyl-4-(4-trifluoromethoxy-phenyl)-piperazine-1-sulfonyl]-indan-2-carboxylic acid tosylate (hereinafter optionally referred to as "Compound 1 tosylate") was used for this experiment instead of Compound 1 tosylate due to the unsuitability of the Compound 1 tosylate crystals for X-ray structure determination. Compound 1 tosylate methyl ester was prepared via an esterification of Compound 1 tosylate followed by recrystallization from isopropanol. Other experiments have established that the stereochemistry is retained in converting the methyl ester to Compound 1 tosylate.

The sample submitted for analysis contained numerous large, well formed rectangular blocks. One such block was trimmed to the dimensions 0.4×0.3×0.3 mm3, coated with mineral oil, picked up on a Nylon loop and chilled to 100 K on the goniometer stage of a Bruker three-axis platform diffractometer equipped with an APEX detector and a KryoCool low-temperature device. All software used in the subsequent data collection, processing and refinement is contained in libraries maintained by Bruker-AXS, Madison, Wis.

From sixty randomly chosen exposures taken in three sequences of twenty exposures at 0.3 deg intervals, it was possible to uniquely assign the crystal to the orthorhombic crystal system with the reported unit cell dimensions. From systematic absences in the diffraction data, it was determined that the particular orthorhombic space group was $P2_12_12$, and, from the volume of the unit cell, that it contained eight molecules. A full hemisphere of data were collected at 100 K yielding 40547 reflections, of which 10238 were crystallographically independent under orthorhombic symmetry providing up to a four-fold redundancy in coverage and a very low merging R factor. The data were first processed by SAINT, a program that integrated the 1,800 individual exposures and prepares a list of reflections and intensities. Corrections were made for absorption, polarization and Lorenzian distortion using SADABS. The structure was solved using direct methods (TREF) and subsequent difference maps were used to locate all non-hydrogen atoms. Refinement using SHELXTL routines for a model incorporating anisotropic thermal parameters for all non-hydrogen atoms and hydrogen atoms as idealized isotropic contributions resulted in a final structure with very low residuals and esd's for bond parameters. Table 1 presents the crystal data and structure refinement for Compound 1 tosylate. Table 2 presents the atomic coordinates and equivalent isotropic displacement parameters for Compound 1 tosylate. Table 3 presents the bond lengths for Compound 1 tosylate. Table 4 presents the bond angles for Compound 1 tosylate.

TABLE 1

| Identification code | Compound 1 Tosylate |
|---|---|
| Empirical formula | C24 H27 F3 N2 O5 S |
| Formula weight | 512.54 |
| Temperature | 100(2) K |
| Wavelength | 0.71073 Å |
| Crystal System | Orthorhombic |
| Space Group | P2(1)2(1)2 |
| Unit Cell Dimensions | a = 17.322(3) Å α = 900<br>b = 25.036(4) Å β = 90°<br>c = 10.8883(18) Å γ = 90° |
| Volume | 472 1.9(13) Å$^3$ |
| Z | 8 |
| Density (calculated) | 1.442 g/cm$^3$ |
| Absorption Coefficient | 0.200 mm$^{-1}$ |
| F(000) | 2144 |
| Crystal Size | 0.40 × 0.30 × 0.30 mm$^3$ |
| Theta range for data collection | 1.43 to 27.61° |
| Index Ranges | −21 ≦ h ≦ 21, −31 ≦ k ≦ 31,<br>−13 ≦ 1 ≦ 13 |
| Reflections Collected | 40547 |
| Independent Reflections | 10238 [R(int) = 0.0318] |
| Completeness to theta = 27.61° | 95.70% |
| Absorption correction | 0.200 mm$^{-1}$ |
| Max. and min. transmission | 0.9424 and 0.9242 |
| Refinement method | Full-matrix least-squares on F2 |
| Data/restraints/parameters | 10238/0/631 |
| Goodness-of-fit on F2 | 1.026 |
| Final R indices [1 > 2 sigma(I)]° | R1 = 0.0344, wR2 = 0.0914 |
| R indices (all data) | R1 = 0.0373, wR2 = 0.0930 |
| Absolute structure parameter | 0.03(4) |

TABLE 2

| | x | y | z | U(eq) |
|---|---|---|---|---|
| S(1) | 8077(1) | 3662(1) | 3670(1) | 17(1) |
| S(1') | 2973(1) | 3589(1) | −8615(1) | 19(1) |
| F(1) | 12175(1) | 4789(1) | −4796(1) | 37(1) |
| F(1') | 6004(1) | 4999(1) | −582(1) | 52(1) |
| F(2') | 7218(1) | 4842(1) | −411(1) | 38(1) |

TABLE 2-continued

| | x | y | z | U(eq) |
|---|---|---|---|---|
| F(2) | 11782(1) | 5189(1) | −3162(1) | 38(1) |
| F(3') | 6773(1) | 5256(1) | −1993(1) | 43(1) |
| F(3) | 10979(1) | 4991(1) | −4587(1) | 38(1) |
| O(1) | 6577(1) | 4385(1) | −1742(1) | 27(1) |
| O(1') | 11507(1) | 4332(1) | −3503(1) | 28(1) |
| O(2) | 7363(1) | 3950(1) | 3590(1) | 22(1) |
| O(2') | 2239(1) | 3841(1) | −8433(1) | 24(1) |
| O(3') | 3307(1) | 3584(1) | −9822(1) | 27(1) |
| O(3) | 8472(1) | 3642(1) | 4827(1) | 23(1) |
| O(4) | 6185(1) | 3206(1) | −901(1) | 47(1) |
| O(4') | 199(1) | 2692(1) | −5704(1) | 32(1) |
| O(5) | 5166(1) | 2750(1) | −220(1) | 30(1) |
| O(5') | 700(1) | 2883(1) | −3860(1) | 25(1) |
| N(1) | 9584(1) | 4134(1) | 625(1) | 18(1) |
| N(1') | 4574(1) | 4142(1) | −5757(1) | 18(1) |
| N(2) | 8649(1) | 3903(1) | 2633(1) | 17(1) |
| N(2') | 3574(1) | 3857(1) | −7655(1) | 19(1) |
| C(1') | 6049(1) | 4342(1) | −2736(2) | 21(1) |
| C(1) | 11000(1) | 4301(1) | −2471(2) | 20(1) |
| C(2) | 11327(1) | 4232(1) | −1324(2) | 22(1) |
| C(2') | 6348(1) | 4293(1) | −3901(2) | 21(1) |
| C(3') | 5849(1) | 4227(1) | −4885(2) | 19(1) |
| C(3) | 10847(1) | 4176(1) | −316(2) | 20(1) |
| C(4) | 10046(1) | 4188(1) | −444(2) | 17(1) |
| C(4') | 5052(1) | 4204(1) | −4707(2) | 17(1) |
| C(S) | 9734(1) | 4259(1) | −1616(2) | 20(1) |
| C(S) | 4765(1) | 4250(1) | −3515(2) | 21(1) |
| C(6') | 5264(1) | 4316(1) | −2523(2) | 24(1) |
| C(6) | 10214(1) | 4315(1) | −2637(2) | 23(1) |
| C(7') | 4716(1) | 3653(1) | −6463(2) | 20(1) |
| C(7) | 9732(1) | 3651(1) | 1352(2) | 19(1) |
| C(8) | 9460(1) | 3724(1) | 2673(2) | 18(1) |
| C(8') | 4394(1) | 3705(1) | −7762(2) | 19(1) |
| C(9) | 8395(1) | 4325(1) | 1769(2) | 16(1) |
| C(9') | 3342(1) | 4296(1) | −6820(2) | 18(1) |
| C(10') | 3748(1) | 4217(1) | −5583(2) | 18(1) |
| C(10) | 8759(1) | 4223(1) | 506(2) | 18(1) |
| C(11) | 7916(1) | 2991(1) | 3218(2) | 16(1) |
| C(11') | 2897(1) | 2913(1) | −8151(2) | 19(1) |
| C(12') | 3378(1) | 2540(1) | −8716(2) | 22(1) |
| C(12) | 8369(1) | 2595(1) | 3768(2) | 19(1) |
| C(13') | 3345(1) | 2007(1) | −8366(2) | 25(1) |
| C(13) | 8289(1) | 2067(1) | 3397(2) | 21(1) |
| C(14) | 7749(1) | 1923(1) | 2519(2) | 22(1) |
| C(14') | 2832(1) | 1838(1) | −7471(2) | 24(1) |
| C(15) | 7291(1) | 2317(1) | 1996(2) | 19(1) |
| C(15') | 2350(1) | 2210(1) | −6918(2) | 20(1) |
| C(16) | 6669(1) | 2255(1) | 1039(2) | 23(1) |
| C(16') | 1722(1) | 2113(1) | −5992(2) | 21(1) |
| C(17') | 1576(1) | 2677(1) | −5454(2) | 20(1) |
| C(17) | 6235(1) | 2801(1) | 1106(2) | 23(1) |
| C(18') | 1802(1) | 3065(1) | −6499(2) | 21(1) |
| C(18) | 6845(1) | 3198(1) | 1557(2) | 22(1) |
| C(19) | 7380(1) | 2854(1) | 2319(2) | 18(1) |
| C(19') | 2389(1) | 2750(1) | −7231(2) | 17(1) |
| C(20) | 11602(1) | 4816(1) | −3989(2) | 28(1) |

TABLE 2-continued

| | x | y | z | U(eq) |
|---|---|---|---|---|
| C(20') | 6631(1) | 4857(1) | −1200(2) | 30(1) |
| C(21') | 4868(1) | 4077(1) | −8577(2) | 25(1) |
| C(21) | 9980(1) | 4095(1) | 3421(2) | 23(1) |
| C(22) | 8570(1) | 4886(1) | 2219(2) | 21(1) |
| C(22') | 3488(1) | 4849(1) | −7354(2) | 22(1) |
| C(23') | 750(1) | 2748(1) | −5048(2) | 21(1) |
| C(23) | 5875(1) | 2947(1) | −108(2) | 25(1) |
| C(24) | 4791(1) | 2862(1) | −1389(2) | 34(1) |
| C(24') | −75(1) | 2959(1) | 3404(2) | 28(1) |

TABLE 3

| Bond | Length, Å | Bond | Length, Å |
|---|---|---|---|
| S(1)—O(2) | 1.4327(12) | C(2)—C(3) | 1.384(2) |
| S(1)—O(3) | 1.4352(12) | C(2')—C(3') | 1.387(2) |
| S(1)—N(2) | 1.6186(14) | C(3')—C(4') | 1.395(2) |
| S(1)—C(11) | 1.7737(16) | C(3)—C(4) | 1.396(2) |
| S(1')—O(2') | 1.4336(12) | C(4)—C(5) | 1.397(2) |
| S(1')—O(3') | 1.4363(13) | C(4')—C(S') | 1.395(2) |
| S(1')—N(2') | 1.6206(14) | C(5)—C(6) | 1.395(2) |
| S(1')—C(11') | 1.7716(17) | C(5')—C(6') | 1.393(2) |
| F(1)—C(20) | 1.328(2) | C(7')—C(8') | 1.526(2) |
| F(1')—C(20') | 1.327(2) | C(7)—C(8) | 1.525(2) |
| F(2')—C(20') | 1.331(2) | C(8)—C(21) | 1.530(2) |
| F(2)—C(20) | 1.333(2) | C(8')—C(21') | 1.527(2) |
| F(3')—C(20') | 1.343(2) | C(9)—C(22) | 1.519(2) |
| F(3)—C(20) | 1.334(2) | C(9)—C(10) | 1.534(2) |
| O(1')—C(20') | 1.325(2) | C(9')—C(22') | 1.524(2) |
| O(1')—C(1') | 1.4214(19) | C(9')—C(10') | 1.532(2) |
| O(1)—C(20) | 1.334(2) | C(11)—C(19) | 1.393(2) |
| O(1)—C(1) | 1.4281(19) | C(11)—C(12) | 1.399(2) |
| O(4)—C(23) | 1.207(2) | C(11')—C(19') | 1.394(2) |
| O(4)—C(23') | 1.200(2) | C(11')—C(12') | 1.395(2) |
| O(5)—C(23) | 1.328(2) | C(12')—C(13) | 1.389(2) |
| O(5)—C(24) | 1.456(2) | C(12)—C(13) | 1.388(2) |
| O(5')—C(23') | 1.340(2) | C(13')—C(14') | 1.385(3) |
| O(5')—C(24') | 1.444(2) | C(13)—C(14) | 1.385(2) |
| N(1)—C(4) | 1.418(2) | C(14)—C(15) | 1.388(2) |
| N(1)—C(10) | 1.453(2) | C(14')—C(15') | 1.387(2) |
| N(1)—C(7) | 1.467(2) | C(15)—C(19) | 1.400(2) |
| N(1')—C(4') | 1.421(2) | C(15)—C(16) | 1.507(2) |
| N(1')—C(10') | 1.456(2) | C(15')—C(19') | 1.396(2) |
| N(1')—C(7') | 1.465(2) | C(15')—C(16') | 1.503(2) |
| N(2)—C(8) | 1.4757(19) | C(16)—C(17) | 1.562(2) |
| N(2)—C(9) | 1.481(2) | C(16')—C(17') | 1.550(2) |
| N(2')—C(8') | 1.475(2) | C(17')—C(23') | 1.508(2) |
| N(2')—C(9') | 1.482(2) | C(17')—C(18') | 1.546(2) |
| C(1')—C(2') | 1.376(2) | C(17)—C(23) | 1.506(2) |
| C(1')—C(6') | 1.380(2) | C(17)—C(18) | 1.531(2) |
| C(1)—C(6) | 1.374(3) | C(18')—C(19') | 1.514(2) |
| C(1)—C(2) | 1.382(3) | C(18)—C(19) | 1.511(2) |

TABLE 4

| Bond | Angle, ° | Bond | Angle, ° |
|---|---|---|---|
| O(2)—S(1)—O(3) | 118.86(8) | C(22)—C(9)—C(10) | 111.24(13) |
| O(2)—S(1)—N(2) | 107.41(7) | N(2')—C(9')—C(22') | 113.32(14) |
| O(3)—S(1)—N(2) | 109.45(7) | N(2)—C(9')—C(10') | 108.65(12) |
| O(2)—S(1)—C(11) | 108.90(7) | C(22)—C(9')—C(10') | 112.10(13) |
| O(3)—S(1)—C(11) | 106.57(7) | N(1')—C(10')—C(9') | 110.68(13) |
| N(2)—S(1)—C(11) | 104.80(7) | N(1)—C(10)—C(9) | 110.45(13) |
| O(2)—S(1')—O(3') | 119.20(8) | C(19)—C(11)—C(12) | 120.04(15) |
| O(2')—S(1')—N(2) | 107.42(7) | C(19)—C(11)—S(1) | 122.16(12) |
| O(3')—S(1')—N(2') | 109.51(8) | C(12)—C(11)—S(1) | 117.76(13) |
| O(2')—S(1')—C(11') | 108.40(7) | C(19')—C(11')—C(12') | 119.80(15) |
| O(3')—S(1')—C(11') | 106.44(8) | C(19')—C(11')—S(1') | 122.17(12) |
| N(2')—S(1')—C(11') | 104.99(7) | C(12')—C(11')—S(1') | 118.02(13) |
| C(20')—O(1')—C(1') | 116.85(13) | C(13')—C(12')—C(11') | 119.85(16) |

TABLE 4-continued

| Bond | Angle, ° | Bond | Angle, ° |
|---|---|---|---|
| C(20)—O(1)—C(1) | 115.87(13) | C(13)—C(12)—C(11) | 119.64(16) |
| C(23)—O(5)—C(24) | 114.96(14) | C(12')—C(13')—C(14') | 120.85(16) |
| C(23')—O(5')—C(24') | 115.20(14) | C(12)—C(13)—C(14) | 121.09(15) |
| C(4)—N(1)—C(10) | 117.82(14) | C(15)—C(14)—C(13) | 118.91(15) |
| C(4)—N(1)—C(7) | 115.03(12) | C(15')—C(14')—C(13') | 119.14(16) |
| C(10)—N(1)—C(7) | 110.23(13) | C(14)—C(15)—C(19) | 121.20(16) |
| C(4')—N(1')—C(10') | 116.99(14) | C(14)—C(15)—C(16) | 128.27(15) |
| C(4')—N(1')—C(7) | 114.59(13) | C(19)—C(15)—C(16) | 110.53(14) |
| C(10')—N(1')—C(7') | 110.00(13) | C(14')—C(15')—C(19') | 120.94(16) |
| C(8)—N(2)—C(9) | 121.21(13) | C(14')—C(15')—C(16') | 128.19(16) |
| C(8)—N(2)—S(1) | 116.69(11) | C(19')—C(15')—C(16') | 110.82(14) |
| C(9)—N(2)—S(1) | 121.78(11) | C(15)—C(16)—C(17) | 102.80(13) |
| C(8')—N(2')—C(9') | 120.03(13) | C(15')—C(16')—C(17') | 102.93(13) |
| C(8')—N(2)—S(1') | 117.51(11) | C(23')—C(17')—C(18') | 112.40(14) |
| C(9')—N(2')—S(1') | 121.86(11) | C(23')—C(17')—C(16') | 111.90(14) |
| C(2')—C(1')—C(6') | 121.47(16) | C(18')—C(17')—C(16') | 104.64(13) |
| C(2')—C(P)—O(1') | 117.75(14) | C(23)—C(17)—C(18) | 114.25(15) |
| C(6')—C(1')—O(1') | 120.65(16) | C(23)—C(17)—C(16) | 111.73(14) |
| C(6)—C(1)—C(2) | 121.86(16) | C(18)—C(17)—C(16) | 104.57(14) |
| C(6)—C(1)—O(1) | 120.28(16) | C(19')—C(18')—C(17') | 103.31(13) |
| C(2)—C(1)—O(1) | 117.79(15) | C(19)—C(18)—C(17) | 103.26(13) |
| C(1)—C(2)—C(3) | 118.90(15) | C(11)—C(19)—C(15) | 119.05(15) |
| C(1)—C(2')—C(3') | 119.21(15) | C(11)—C(19)—C(18) | 130.90(15) |
| C(2')—C(3)—C(4') | 120.96(16) | C(15)—C(19)—C(18) | 110.04(14) |
| C(2)—C(3)—C(4) | 121.05(16) | C(11')—C(19')—C(15') | 119.37(15) |
| C(5)—C(4)—C(3) | 118.60(16) | C(11')—C(19')—C(18') | 130.45(15) |
| C(5)—C(4)—N(1) | 122.97(15) | C(15')—C(19')—C(18') | 110.09(14) |
| C(3)—C(4)—N(1) | 118.43(15) | F(1)—C(20)—F(2) | 107.96(15) |
| C(5)—C(4')—C(3') | 118.60(15) | F(1)—C(20)—O(1) | 107.93(15) |
| C(5')—C(4')—N(1') | 123.37(15) | F(2)—C(20)—O(1) | 113.46(15) |
| C(3)—C(4')—N(1') | 118.02(15) | F(1)—C(20)—F(3) | 107.35(14) |
| C(6)—C(5)—C(4) | 120.69(15) | F(2)—C(20)—F(3) | 106.83(15) |
| C(6')—C(5')—C(4') | 120.65(15) | O(1)—C(20)—F(3) | 113.04(16) |
| C(1')—C(6')—C(5') | 119.10(16) | O(1')—C(20')—F(1') | 114.08(17) |
| C(1)—C(6)—C(5) | 118.90(16) | O(1')—C(20')—F(2') | 108.41(15) |
| N(1')—C(7')—C(8') | 110.72(13) | F(1')—C(20')—F(2') | 107.79(15) |
| N(1)—C(7)—C(8) | 110.88(13) | O(1')—C(20')—F(3') | 112.95(16) |
| N(2)—C(8)—C(7) | 107.60(13) | F(1')—C(20')—F(3') | 106.07(16) |
| N(2)—C(8)—C(21) | 113.06(14) | F(2')—C(20')—F(3') | 107.22(15) |
| C(7)—C(8)—C(21) | 113.12(14) | O(4')—C(23')—O(5') | 123.55(16) |
| N(2')—C(8')—C(7') | 107.50(13) | O(4')—C(23')—C(17') | 124.49(16) |
| N(2')—C(8')—C(21') | 113.94(14) | O(5')—C(23')—C(17') | 111.97(14) |
| C(7')—C(8')—C(21') | 113.22(14) | O(4)—C(23)—0(5) | 122.99(17) |
| N(2)—C(9)—C(22) | 113.35(13) | O(4)—C(23)—C(17) | 125.01(17) |
| N(2)—C(9)—C(10) | 109.16(12) | O(5)—C(23)—C(17) | 112.01(15) |

Biological Activity Assay

Compounds 1 and 2 were assayed to measure their biological activity with respect to $EC_{50}$ values and efficacy for modulating PPARα, PPARγ, and PPARδ as set forth below. Compounds were screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same synthetic response element and to prevent endogenous receptor activation from complicating the interpretation of results. See, for example, Lehmann, J. M.; Moore, L. B.; Smith-Oliver, T. A; Wilkinson, W. O.; Willson, T. M.; Kliewer, S. A., An antidiabetic thiazolidinedione is a high affinity ligand for peroxisome proliferator-activated receptor δ (PPARδ), *J. Biol. Chem.,* 1995, 270, 12953-6. The ligand binding domains for murine and human PPARα, PPARγ, and PPARδ are each fused to the yeast transcription factor GAL4 DNA binding domain. CV-1 cells were transiently transfected with expression vectors for the respective PPAR chimera along with a reporter construct containing four or five copies of the GAL4 DNA binding site driving expression of luciferase. After 8-16 h, the cells are replated into multi-well assay plates and the media is exchanged to phenol-red free DME medium supplemented with 5% delipidated calf serum. 4 hours after replating, cells were treated with either compounds or 1% DMSO for 20-24 hours. Luciferase activity was then assayed with Britelite (Perkin Elmer) following the manufacturer's protocol and measured with either the Perkin Elmer Viewlux or Molecular Devices Acquest (see, for example, Kliewer, S. A., et. al. Cell 1995, 83, 813-819). Rosiglitazone is used as a positive control in the PPARγ assay. Wy-14643 and GW7647 is used as a positive control in the PPARα assay. GW501516 is used as the positive control in the PPARδ assay. Results are shown in Table 5 below:

TABLE 5

| Compound | PPAR alpha A = >100 μM B = 5-100 μM C = <5 μM | PPAR delta A = >100 μM B = 5-100 μM C = <5 μM | PPAR gamma A = >100 μM B = 5-100 μM C = <5 μM |
|---|---|---|---|
| 1 | A | C | A |
| 2 | A | C | B |

This table is adapted from Table 1 in US2006/0205736, published Sep. 14, 2006, the disclosure of which is hereby incorporated by reference as if written herein in its entirety.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A salt of a compound of Formula I,

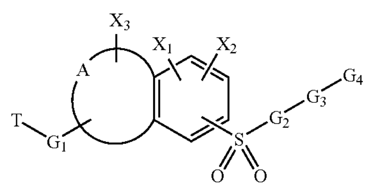

(I)

wherein:

A is a saturated or unsaturated hydrocarbon chain or a heteroatom-comprising hydrocarbon chain having from 3 to 5 atoms, forming a five- to seven-membered ring;

T is selected from the group consisting of —C(O)OH, —C(O)$NH_2$, and tetrazole;

$G_1$ is selected from the group consisting of —$(CR^1R^2)_n$—, —$Z(CR^1R^2)_n$—, —$(CR^1R^2)_nZ$—, —$(CR^1R^2)_rZ(CR^1R^2)_s$—;

Z is O, S or NR;

n is 0, 1, or 2;

r and s are 0 or 1;

$R^1$ and $R^2$ are independently selected from the group consisting of hydrogen, halo, optionally substituted lower alkyl, optionally substituted lower heteroalkyl, optionally substituted lower alkoxy, and lower perhaloalkyl or together may form an optionally substituted cycloalkyl;

$X_1$, $X_2$, and $X_3$ are independently selected from the group consisting of hydrogen, optionally substituted lower alkyl, optionally substituted cycloalkyl, halogen, perhaloalkyl, hydroxy, optionally substituted lower alkoxy, nitro, cyano, and $NH_2$;

$G_2$ is selected from the group consisting of a saturated or unsaturated cycloalkyl or heterocycloalkyl linker, optionally substituted with $X_4$ and $X_5$;

$X_4$ and $X_5$ are independently selected from the group consisting of hydrogen, optionally substituted lower alkyl, halogen, lower perhaloalkyl, hydroxy, optionally substituted lower alkoxy, nitro, cyano, $NH_2$, and $CO_2R$;

R is selected from the group consisting of lower alkyl and hydrogen;

$G_3$ is selected from the group consisting of a bond, a double bond, —$(CR^3R^4)_m$—, carbonyl, and —$(CR^3R^4)_mCR^3$=$CR^4$—;

m is 0, 1, or 2;

$R^3$ and $R^4$ are independently selected from the group consisting of hydrogen, optionally substituted lower alkyl, optionally substituted lower alkoxy, optionally substituted aryl, lower perhaloalkyl, cyano, and nitro;

$G_4$ is selected from the group consisting of hydrogen, optionally substituted aryl, optionally substituted heteroaryl, optionally substituted cycloalkyl, optionally substituted heterocycloalkyl, optionally substituted cycloalkenyl, and —N=$(CR^5R^6)$; and $R^5$ and $R^6$ are independently selected from the group consisting of hydrogen, optionally substituted aryl, optionally substituted heteroaryl, optionally substituted cycloalkyl, optionally substituted cycloalkenyl, and optionally substituted heterocycloalkyl;

and wherein said salt is selected from the group consisting of sulfate, sodium, potassium, magnesium, calcium, hydrochloride, phosphonate, and tosylate.

2. The salt as recited in claim 1, wherein the salt is tosylate salt of said compound.

3. The salt as recited in claim 1 wherein the compound is 4-[cis-2,6-dimethyl-4-(4-trifluoromethoxy-phenyl)-piperazine-1-sulfonyl]-indan-2-carboxylic acid.

4. The salt as recited in claim 3, wherein said compound is 4-[cis-2,6-dimethyl-4-(4-trifluoromethoxy-phenyl)-piperazine-1-sulfonyl]-indan-2-carboxylic acid.

5. (S)-4-[cis-2,6-dimethyl-4-(4-trifluoromethoxy-phenyl)-piperazine-1-sulfonyl]-indan-2-carboxylic acid tosylate.

6. A pharmaceutical composition comprising a salt as recited in claim 1, together with a pharmaceutically acceptable diluent or carrier.

7. A pharmaceutical composition comprising a salt as recited in claim 5, together with a pharmaceutically acceptable diluent or carrier.

8. The salt as recited in claim 1 wherein the compound is 4-[cis-2,6-dimethyl-4-(4-trifluoromethoxy-benzyl)-piperazine-1-sulfonyl]-indan-2-carboxylic acid.

9. The salt as recited in claim 2 wherein the compound is 4-[cis-2,6-dimethyl-4-(4-trifluoromethoxy-benzyl)-piperazine-1-sulfonyl]-indan-2-carboxylic acid.

* * * * *